United States Patent
Sun

(10) Patent No.: US 7,985,751 B2
(45) Date of Patent: Jul. 26, 2011

(54) PIPERAZINE DERIVATIVES

(75) Inventor: Connie Sun, Palo Alto, CA (US)

(73) Assignee: M's Science Corporation, Minatojima-minamimachi, Chuo-ku, Kobe (JP)

( * ) Notice: Subject to any disclaimer, the term of this patent is extended or adjusted under 35 U.S.C. 154(b) by 50 days.

(21) Appl. No.: 11/989,952

(22) PCT Filed: Aug. 2, 2006

(86) PCT No.: PCT/US2006/030072
§ 371 (c)(1),
(2), (4) Date: Feb. 4, 2008

(87) PCT Pub. No.: WO2007/021545
PCT Pub. Date: Feb. 22, 2007

(65) Prior Publication Data
US 2009/0143395 A1    Jun. 4, 2009

Related U.S. Application Data

(60) Provisional application No. 60/707,115, filed on Aug. 9, 2005.

(51) Int. Cl.
*C07D 241/04* (2006.01)
*A61K 31/50* (2006.01)
(52) U.S. Cl. .................. 514/252.12; 544/358
(58) Field of Classification Search .................. 544/358; 514/252.12
See application file for complete search history.

(56) References Cited

U.S. PATENT DOCUMENTS

| | | |
|---|---|---|
| 5,389,630 A | 2/1995 | Sato et al. |
| 5,736,546 A | 4/1998 | Kawashima et al. |
| 2003/0171347 A1* | 9/2003 | Matsumoto .................. 514/183 |

FOREIGN PATENT DOCUMENTS

| WO | WO 91/09594 | 7/1991 |
|---|---|---|
| WO | WO 2004/110387 | 12/2004 |

OTHER PUBLICATIONS

Kazunori Kawamura et al., "Improved syntheis . . . " Annals of Nuclear Medicine, vol. 18, No. 2, 165-1168, 2004.*
Matsumoto et al., "Structure-activity comparison . . . ", Pharmacology Biochemistry & Behavior 77 (2004) 775-581.*
Fujimura et al., "Synthesis, Structure . . . " Bio & Med Chem, vol. 5, No. 8 pp. 1675-1683, 1997.*
Elsinga et al., "Evaluation of Fluorinated sigma receptor . . . ", Synapse 52:29-37 2004.*

* cited by examiner

*Primary Examiner* — Paul V. Ward
(74) *Attorney, Agent, or Firm* — Paul N. King

(57) ABSTRACT

Compounds of general formula (I)

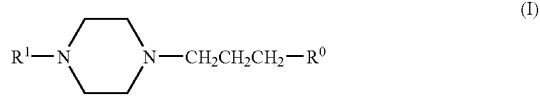

in which $R^1$ and $R^0$ have any of the meanings given in the specification have affinity for sigma receptors and are useful in the treatment of disorders of the central nervous system.

13 Claims, No Drawings

PIPERAZINE DERIVATIVES

This application claims priority based on U.S. provisional application No. 60/707,115 filed Aug. 9, 2005, entitled "Piperazine Derivatives," which is hereby incorporated herein by reference in the entirety of its disclosure.

BACKGROUND

The present invention relates to novel piperazine derivatives, to processes for preparing the novel piperazine derivatives, to novel intermediates useful in the process, to pharmaceutical compositions comprising piperazine derivatives, and to the use of piperazine derivatives in the treatment of disorders of the central nervous system.

It has been disclosed in the scientific literature that certain disorders of the central nervous system may be treated using a modulator of sigma receptor function. Amongst compounds known to possess affinity for sigma ligands are certain piperazine derivatives.

WO 91/09594 discloses compounds having affinity for sigma receptors, certain of which are piperazine derivatives, and discloses that they are useful in the treatment of schizophrenia and other psychoses.

U.S. Pat. No. 5,736,546 discloses certain 1,4-(diphenylalkyl)piperazines having one phenyl group unsubstituted and the other phenyl group substituted by two alkoxy groups. One of the compounds disclosed is 1-[2-(3,4-dimethoxyphenyl)ethyl]-4-(3-phenylpropyl)piperazine. It is also referred to in the scientific literature as SA 4503. The compounds of U.S. Pat. No. 5,736,546 are said to be useful in the treatment of dementia, depression, schizophrenia, anxiety neurosis, diseases accompanying abnormal immune response, cryptorrhea and digestive ulcer.

WO 2004/110387 discloses that sigma ligands, in particular SA 4503, are also useful in the treatment of patients to facilitate neuronal regeneration after onset of a neurodegenerative disease, such as ischemic stroke, traumatic brain injury, or spinal chord injury.

Many 1,4-(diphenylalkyl)piperazines have been disclosed, generically or specifically, although mostly not as sigma ligands. For example, U.S. Pat. No. 5,389,630 generically discloses that certain diamine compounds possess cerebral protective action. The compound 1-[2-(3,4,5-trimethoxyphenyl)ethyl]-4-(3-phenylpropyl)piperazine is commercially available, but is not believed to have any known pharmaceutical use.

It has now been found that certain 1,4-(diphenylalkyl)piperazines, including the known compound 1-[2-(3,4,5-trimethoxyphenyl)ethyl]-4-(3-phenylpropyl)piperazine, have high affinity for sigma receptors, in particular sigma-1 receptors.

DESCRIPTION OF ILLUSTRATIVE EMBODIMENTS

According to one aspect, the present invention provides a compound of general formula (I)

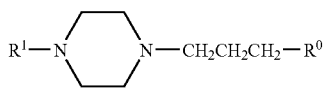

(I)

in which:—
$R^0$ represents phenyl or 4-fluorophenyl; and
$R^1$ represents:—
(i) a group of formula $$R^2-(CH_2)_nCH_2-$$

wherein:—
n is 1 or 2; and
$R^2$ represents a phenyl group that is substituted by one, two, or three substituents selected independently from (1-2C)alkylenedioxy, a halogen atom, a hydroxyl group, a (1-4C) alkyl group, a (3-6C)cycloalkyl group, a halo(1-4C) alkyl group, a (1-4C)alkoxy group, and a halo(1-4C)alkoxy group, provided that when $R^0$ represents phenyl, $R^2$ is not 3,4,5-trimethoxyphenyl or phenyl substituted by two (1-4C) alkoxy groups;
(ii) a group of formula $$R^3-(CH_2)_mC(R^{4a}R^{4b})-$$

wherein:—
m is 1 or 2;
$R^3$ represents a phenyl group that is unsubstituted or substituted by one, two, or three substituents selected independently from (1-2C)alkylenedioxy, a halogen atom, a hydroxyl group, a (1-4C) alkyl group, a (3-6C)cycloalkyl group, a halo(1-4C) alkyl group, a (1-4C)alkoxy group, and a halo(1-4C)alkoxy group; and
one or two of $R^{4a}$ and $R^{4b}$ represents a (1-4C) alkyl or a (1-4C)alkoxy(1-4C)alkyl group and any remainder represents a hydrogen atom; or
(iii) indan-1-yl, indan-2-yl, 1,2,3,4-tetrahydronaphth-1-yl or 1,2,3,4-tetrahydronaphth-2-yl, each of which may bear a hydroxyl substituent on a non-aromatic carbon atom, or (3-6C) cycloalkyl;
or a pharmaceutically acceptable salt thereof.

Compounds according to the invention, and the known compound 1-[2-(3,4,5-trimethoxyphenyl)ethyl]-4-(3-phenylpropyl)piperazine, have been found to have high affinity for sigma receptors, in particular sigma-1 receptors.

As used herein, unless otherwise indicated, the term halogen atom includes fluorine, chlorine, and bromine.

The term (1-2C)alkylenedioxy includes methylenedioxy and ethylenedioxy.

An example of a (1-4C) alkyl group is methyl. Other examples are ethyl, propyl, 2-propyl, butyl, 2-butyl, and t-butyl.

The term halo(1-4C)alkyl as used herein includes perfluoro(1-4C)alkyl, such as trifluoromethyl.

An example of a (1-4C)alkoxy group is methoxy. Other examples are ethoxy, propoxy, and 2-propoxy.

The term halo(1-4C)alkoxy as used herein includes perfluoro(1-4C)alkoxy, such as trifluoromethoxy.

Examples of a (3-6C) cycloalkyl group are cyclopentyl and cyclohexyl.

An example of a particular value for $R^0$ is phenyl.
An example of a particular value for n is 1.
An example of a particular value for m is 1.
Examples of particular values for $R^2$ are 3-methoxy-4-hydroxyphenyl, 3,4-dihydroxyphenyl, 3,4-methylenedioxyphenyl (benzo[1,3]dioxol-5-yl), 2-fluorophenyl, 3-fluorophenyl, 4-fluorophenyl, 3,4-difluorophenyl, 3-methylphenyl, 3-trifluoromethylphenyl, 2-trifluoromethoxyphenyl, 3-chloro-4-methoxyphenyl, and 2-fluoro-6-chlorophenyl. Other examples of particular values for $R^2$ are 2-methoxyphenyl, 2-fluoro-3,4-dimethoxyphenyl, 2,3,4-Trimethoxyphenyl, 2-trifluoromethylphenyl, 4-trifluoromethylphenyl, 3-trifluoromethoxyphenyl, 3-chlorophenyl, 2-fluoro-4,5-dimethoxyphenyl, 2-fluoro-4-methoxy-5-hydroxyphenyl, 3-bromo-4,5-dimethoxyphenyl, 3-bromo-4-ethoxy-5-methoxyphenyl, 3-bromo-4-methoxy-5-ethoxyphenyl, 3-methoxy-4-isopropoxyphenyl, 3-fluoro-4,5-dimethoxyphenyl, 3,5-dimethoxy-4-hydroxyphenyl, 3-bromo-4-hydroxy-5-methoxyphenyl, 3,4-dimethoxy-5-hydroxyphenyl, 2-chloro-3,4-dimethoxyphenyl, 3-isopropyl-4-methoxyphenyl, 7-fluorobenzo[1,3]dioxol-5-yl, 3-chloro-4-methoxy-5-isopropylphenyl, 4-cyclohexyl-3-methoxyphenyl, and 2-chloro-3-methoxy-4-hydroxyphenyl.

For $R^2$, particular mention may be made of the fluorophenyl groups, especially 2-fluorophenyl.

Examples of particular values for $R^3$ are phenyl, 3,4-dimethoxyphenyl, 3-methoxy-4-hydroxyphenyl, 3,4-dihydroxyphenyl, 3,4-methylenedioxyphenyl, 2-fluorophenyl, 3-fluorophenyl, 4-fluorophenyl, 3,4-difluorophenyl, 3-methylphenyl, 3-trifluoromethylphenyl, 2-trifluoromethoxyphenyl, 3-chloro-4-methoxyphenyl, and 2-fluoro-6-chlorophenyl. A particular example of a value for $R^3$ is phenyl.

Examples of particular values for $R^{4a}$ and $R^{4b}$ are:—
for an alkyl group: methyl; and
for a (1-4C)alkoxy(1-4C)alkyl group: methoxymethyl.

For example, $R^{4a}$ may represent methoxymethyl and $R^{4b}$ a hydrogen atom, or $R^{4a}$ and $R^{4b}$ may each represent a methyl group.

Examples of particular values for $R^1$ are indan-1-yl, 2-hydroxyindan-1-yl, indan-2-yl, 1,2,3,4-tetrahydronaphth-1-yl, 1,2,3,4-tetrahydronaphth-2-yl, cyclopentyl, and cyclohexyl. Other examples for $R^1$ are indan-2-yl, 1(S)-indan-1-yl, (1R,2S)-(2-hydroxyindan-1-yl),
(1S,2R)-(2-hydroxyindan-1-yl), (1R)-(1,2,3,4-tetrahydronaphthalen-1-yl,
(1S)-(1,2,3,4-tetrahydronaphthalen-1-yl), cyclopentyl, and (1S,2S)-(2-hydroxycyclopent-1-yl).

For example $R^1$ may represent indan-1-yl.

In one embodiment of the invention, $R^1$ represents:—
a group of formula

$R^2$—CH$_2$CH$_2$—

It will be appreciated that the compounds of formula (I) may contain a centre of asymmetry. The compounds may therefore exist and be isolated in the form of stereoisomers. The present invention provides a compound of formula (I) in any stereoisomeric form.

It will also be appreciated that the compounds of formula (I) or their pharmaceutically acceptable salts may be isolated in the form of a solvate, and accordingly that any such solvate is included within the scope of the present invention.

Certain compounds of formula (I) have also been found to possess good selectivity for sigma-1 receptors compared with sigma-2 receptors. This is particularly desirable, because the sigma-2 receptors have been shown to play an important role in the sigma receptor-mediated neck dystonia in rats (Matsumoto R R, et al Pharmacol. Biochem. Behav. 36, 151-155, 1996). For example microinjection of DTG (1,3-di-2-tolyl-guanidine, a sigma 1 and sigma 2 receptor agonist) induced neck dystonia in rats while injection of SA-4503 (a selective sigma 1 agonist) had no effect (Nakazawa M et al, Pharmacol Biochem. Behav. 62, 123-126, 1999). In addition sigma 2 receptors have been implicated in the regulation of cell proliferation. Cytotoxic effects have been correlated with sigma 2 receptor ligands (Vilner and Bowen, Eur. J. Pharmacol Mol Pharmacol Sect 244, 199-201, 1993). Sigma 2 selective drugs can inhibit tumor cell proliferation through mechanisms that may involve apoptosis and intracellular calcium release (Aydar E et al, Cancer Research 64, 5029-5035, 2004). These compounds are therefore particularly preferred.

According to another aspect, therefore, the present invention provides a compound which is selected from 1-[2-(2-fluorophenyl)ethyl]-4-(3-phenylpropyl)piperazine;

1-[2-(3-methylphenyl)ethyl]-4-(3-phenylpropyl)piperazine;

and pharmaceutically acceptable salts thereof.

These compounds have both been found to possess good selectivity for sigma-1 over sigma-2 receptors.

The compound 1-[2-(2-fluorophenyl)ethyl]-4-(3-phenylpropyl)piperazine has been found to possess especially good affinity and selectivity for sigma-1 receptors. The compound and its pharmaceutically acceptable salts, including 1-[2-(2-fluorophenyl)ethyl]-4-(3-phenylpropyl)piperazine dihydrochloride, are therefore provided as preferred embodiments of the invention.

The compounds of general formula (I) can be prepared by conventional processes.

According to another aspect, therefore, the present invention provides a process for preparing a compound of general formula (I), or a pharmaceutically acceptable salt thereof, which comprises reacting a compound of general formula (II)

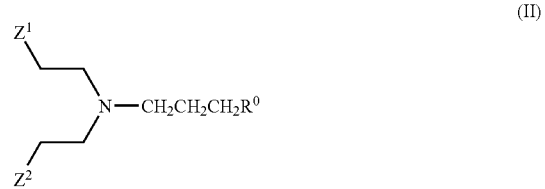

in which each of $Z^1$ and $Z^2$ independently represents a leaving atom or group, with a compound of general formula (III)

$R^1$—NH$_2$ (III)

or a corresponding compound in which one or two substituents on $R^1$ are protected;

followed by removing any protecting group and, optionally, forming a pharmaceutically acceptable salt.

The leaving atoms or groups represented by $Z^1$ and $Z^2$ may be, for example, hydrocarbylsulfonyloxy groups, such as methanesulfonyloxy or p-toluenesulfonyloxy, or halogen atoms, such as chlorine atoms.

The reaction is conveniently performed at a temperature in the range of from 0 to 100° C., such as from 50 to 90° C. Convenient solvents include organic solvents, for example amides such as dimethylformamide. The reaction is conveniently performed in the presence of a base, for example an alkali metal carbonate such as potassium carbonate. The reaction may be performed in the presence of a catalyst, such as sodium iodide.

A pharmaceutically acceptable salt may be formed by a conventional method, such as by reacting a compound of formula (I) with a pharmaceutically acceptable acid, such as hydrochloric acid.

Compounds of formula (II) may be prepared from the corresponding diol of formula (IV).

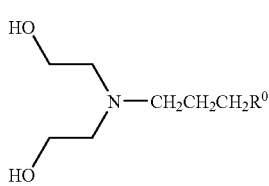

(IV)

For example, a compound of formula (II) in which $Z^1$ and $Z^2$ represent halogen atoms may be prepared by reacting a compound of formula (II) with a halogenating agent, for example a thionyl halide such as thionyl chloride. Convenient solvents include amides, such as dimethylformamide.

Compounds of formula (IV) may be prepared by reacting a compound of formula (V)

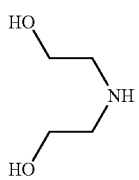

(V)

with a compound of formula (VI)

 (VI)

in which $Z^3$ represents a leaving atom or group, for example a halogen atom such as a bromine atom. The reaction is conveniently performed in the presence of a base, such as potassium carbonate, in a suitable solvent, for example an alcohol such as ethanol, and at an elevated temperature, for example under reflux.

Compounds of formula (III), (V) and (VI) are generally known or commercially available.

Certain of the intermediates, for example certain compounds of formula (II) or (IV) may be novel. The invention also provides all novel intermediates disclosed herein.

The compounds of the invention may be administered by any convenient route, e.g. into the gastrointestinal tract (e.g. rectally or orally), the nose, lungs, musculature or vasculature, or transdermally. The compounds may be administered in any convenient administrative form, e.g. tablets, powders, capsules, solutions, dispersions, suspensions, syrups, sprays, suppositories, gels, emulsions, patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of formula (I) or a pharmaceutically acceptable salt thereof, as defined hereinabove, or a compound selected from 1-[2-(3,4,5-trimethoxyphenyl)ethyl]-4-(3-phenylpropyl)piperazine and pharmaceutically acceptable salts thereof, together with a pharmaceutically acceptable diluent or carrier.

According to another aspect, the present invention provides the compound of formula (I) or a pharmaceutically acceptable salt thereof, or a compound selected from 1-[2-(3,4,5-trimethoxyphenyl)ethyl]-4-(3-phenylpropyl)piperazine and pharmaceutically acceptable salts thereof, for use in therapy.

According to another aspect, the present invention provides the use of the compound of formula (I) or a pharmaceutically acceptable salt thereof, or a compound selected from 1-[2-(3,4,5-trimethoxyphenyl)ethyl]-4-(3-phenylpropyl)piperazine and pharmaceutically acceptable salts thereof, for the manufacture of a medicament for the treatment of a disorder responsive to a modulator of sigma receptor function.

According to another aspect, the present invention provides a method of treating a condition responsive to a modulator of sigma receptor function in a patient requiring treatment, which comprises administering to said patient an effective amount of a compound of formula (I) or a pharmaceutically acceptable salt thereof, or a compound selected from 1-[2-(3,4,5-trimethoxyphenyl)ethyl]-4-(3-phenylpropyl)piperazine and pharmaceutically acceptable salts thereof.

The subject may be a human or a non-human animal, such as a non-human mammal, for example a cat, dog, horse, cow, or sheep.

The disorder responsive to a sigma receptor modulator may be, for example, a disorder of the central nervous system, such as a neurological disorder or a psychiatric disorder that has been linked to sigma receptors. Examples of neurological disorders include cerebral deficits subsequent to cardiac bypass surgery and grafting, cerebral ischemia (e.g. associated with stroke or cardiac arrest); spinal cord trauma; head trauma; multiple sclerosis, Alzheimer's Disease; Huntington's Chorea; amyotrophic lateral sclerosis; AIDS-induced dementia; muscular spasms; convulsions; drug tolerance, withdrawal, and cessation (i.e. opiates, benzodiazepines, nicotine, cocaine, or ethanol); ocular damage and retinopathy; cognitive disorders; idiopathic and drug-induced Parkinson's Disease; pain; and movement disorders such as tardive dyskinesia. Examples of psychiatric disorders that are treated with a compound of formula I include schizophrenia, anxiety and related disorders (e.g. panic attack and stress-related disorders), depression, bipolar disorders, psychosis, and obsessive compulsive disorders.

The compounds according to the invention are of particular interest for use as neuroprotective agents and in the treatment of patients to facilitate neuronal regeneration and functional recovery after onset of a neurodegenerative disease, in particular ischemic stroke, traumatic brain injury, spinal chord injury, and multiple sclerosis.

The dosage of the compounds of formula (I) will depend upon the nature and severity of the condition being treated, the administration route, and the size and species of the subject. In general, quantities in the range of from 0.01 to 100 mg/kg bodyweight will be administered.

As used herein, the term "treatment" includes prophylactic use. The term "effective amount" refers to the amount of the compound of formula (I) that is effective to reduce or inhibit the development of the symptoms of the disorder being treated.

The compound according to the invention may be administered alone or in combination with another therapeutic agent having a different mode of action.

The ability of a compound to bind to a sigma receptor may be demonstrated by one or more of the following tests.

Sigma 1 (σ1) and sigma 2 (σ2) receptor binding assays are carried out in membranes from HEK-293 (Human Embryonic Kidney) cells.

Membrane Preparation:

Confluent HEK-293 cells are harvested in PBS/5 mM EDTA. They are centrifuged at 2000 rpm for 5 min and then washed two times in PBS. Cells are homogenized in 20 mM Tris-HCL (pH=7.5) containing 5 mM EDTA, 0.5 mM PMSF and 0.5 µg/ml leupeptin using a Dounce homogenizer and sonicated for 5 minutes.

Nuclear debris and intact cells are removed by centrifugation at 3000 rpm for 10 minutes at 4° C. The supernatant is centrifuged at 12000 rpm for 30 minutes and the resulting pellet is resuspended in 25 mM Tris-HCL (pH=7.5), 25 mM $Mg_2Cl$, 10% sucrose containing 0.5 mM PMSF, 2 mM AEBSF, 1 mM EDTA, 130 µM bestatin, 14 µM E-64, 1 µM leupeptin, and 0.3 mM aprotinin.

Proteins are determined using the Bio Rad Protein Assay Dye Reagent and the membranes are aliquoted and frozen at −80° C.

σ1 Receptor Binding Assay

The binding assays are performed in 96-well plates.

σ1 receptors are labeled using the σ1 selective probe (+)-[$^3$H] Pentazocine (Bowen W D et al, Mol Neuropharmacol 3, 117-126, 1993).

Total binding is determined by incubating 50 µg of HEK-293 cell membranes with 10 nM (+)-[$^3$H]-pentazocine (Perkin-Elmer, 35 Ci/mmol) and assay buffer (50 mM Tris-HCl, pH=8.3) in a total volume of 200 µl. Non specific binding is determined in the presence of 10 µM unlabeled pentazocine. For competition experiments, 50 µl of displacing compound is added at 8 different concentrations. Incubations are carried out for 120 min at 37° C. Assays are terminated by dilution with ice-cold 10 mM Tris-HCl, pH=8.3 and vacuum filtration through glass fibers using a Skatron cell harvester from Molecular Devices. The filters are washed three times and the membrane-bound radioactivity is determined in a Microbeta scintillation counter.

Filters are soaked in 0.5% polyethyleneimine for 1 hour before use.

Specific binding is determined by subtraction of non specific binding from total binding. $IC_{50}$ values (concentration of competing ligand required for 50% inhibition of [$^3$H]-pentazocine binding) are analyzed by non-linear regression fit using the GraphPad Prism software.

σ2 Receptor Binding Assay

The binding assays are performed in 96-well plates.

σ2 receptors are labeled using [$^3$H] DTG (Di-o-tolylguanidine), under conditions in which σ1 receptors are masked with the σ1 selective compound pentazocine (Hellewell S B et al, Eur. J. Pharmacol, 268, 9-18, 1994).

Total binding is determined by incubating 50 µg of HEK-293 cell membranes with 10 nM [$^3$H]-DTG (Perkin-Elmer, 58 Ci/mmol) in the presence of 10 µM pentazocine and assay buffer (50 mM Tris-HCl, pH=8.3) in a total volume of 200 µl. Non specific binding is determined in the presence of 10 µM unlabeled DTG. For competition experiments, 50 µl of displacing compound is added at 8 different concentrations. Incubations are carried out for 120 min at 37° C. Assays are terminated by dilution with ice-cold 10 mM Tris-HCl, pH=8.3 and vacuum filtration through glass fibers using a Skatron cell harvester from Molecular Devices. The filters are washed three times and the membrane-bound radioactivity is determined in a Microbeta scintillation counter.

Filters are soaked in 0.5% polyethyleneimine for 1 hour before use.

Specific binding is determined by subtraction of non specific binding from total binding. $IC_{50}$ values (concentration of competing ligand required for 50% inhibition of [$^3$H]-DTG binding) are analyzed by non-linear regression fit using the GraphPad Prism software.

The compounds exemplified herein have all been found to have an $IC_{50}$ of less than 300 nM in the σ1 receptor binding assay. The known compound 1-[2-(3,4,5-trimethoxyphenyl)ethyl]-4-(3-phenylpropyl)piperazine hydrochloride has also been found to have an $IC_{50}$ of less than 300 nM in the σ1 receptor binding assay, and to be highly selective for the σ1 receptor over the σ2 receptor.

The following examples illustrate the invention.

Preparation 1

Bis(2-hydroxyethyl)-(3-phenylpropyl)amine

To a solution of (3-bromopropyl)benzene and bis(2-hydroxyethyl)amino in ethanol is added anhydrous potassium carbonate. The mixture is heated under reflux for 8 h, cooled, and filtered. The residue is dissolved in ethyl acetate, washed with saturated sodium bicarbonate and brine, dried over anhydrous magnesium sulfate, and concentrated to give the title compound.

Preparation 2

Bis(2-chloroethyl)-(3-phenylpropyl)ammonium chloride

To an ice-cooled solution of the product of Preparation 1 in dichloromethane (DCM) is added thionyl chloride dropwise, with the temperature being maintained under 10° C. The reaction mixture is then stirred at ambient temperature for 30 minutes, heated under reflux for 1 hour, cooled, and concentrated. Isopropyl ether is then added, and the resulting mixture is concentrated again. The concentrated residue is then dissolved in ethyl acetate and isopropyl ether is added, causing a precipitate to form. The precipitate is collected by filtration and dried in a vacuum oven overnight to give the title compound.

EXAMPLE 1

1-[2-(3-Methoxy-4-hydroxyphenyl)ethyl]-4-(3-phenylpropyl)piperazine dihydrochloride

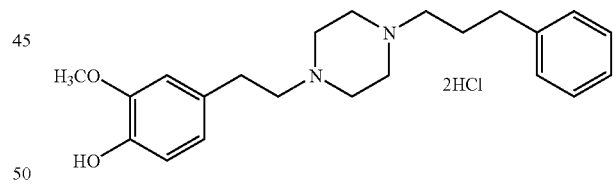

A mixture of bis(2-chloroethyl)-(3-phenylpropyl)ammonium chloride (116 mg, 0.39 mmol), potassium carbonate (119 mg, 0.86 mmol), sodium iodide (134.9 mg, 0.9 mmol), and 2-(4-(benzyloxy)-3-methoxyphenyl)ethanamine hydrochloride (100 mg, 0.34 mmol) in dimethylformamide (3 ml) is stirred at 70° C. for 5 h and then cooled to ambient temperature. To the resultant mixture is added water and ethyl acetate. The organic layer is washed with brine, dried over anhydrous sodium sulfate, and concentrated. The resulting residue is then purified by column chromatography, eluting with methanol-dichloromethane (1:9) to yield 112 mg of 1-(4-(benzyloxy)-3-methoxyphenethyl)-4-(3-phenylpropyl)piperazine (83%).

1-(4-(Benzyloxy)-3-methoxyphenethyl)-4-(3-phenylpropyl)piperazine is hydrogenated in 10 mL methanol with 10% Pd/C. The resultant product is then purified by column chromatography, eluting with dichloromethane-methanol (9:1) to afford 95 mg of 1-[2-(3-methoxy-4-hydroxyphenyl)ethyl]-4-(3-phenylpropyl)piperazine.

To a solution of 1-[2-(3-methoxy-4-hydroxyphenyl)ethyl]-4-(3-phenylpropyl)-piperazine in ethanol is added 6 N hydrogen chloride aqueous solution until the pH is 3. The resulting solution is allowed to stand at ambient temperature overnight. The resultant crystals were filtered, washed with cold ethanol, and dried to give 61 mg of the title compound (57%).

m/z 355 [M+1]$^+$.

$^1$H-NMR (400 MHz, DMSO-d$_6$): δ 2.03 (b, 2H), 2.64 (t, 2H), 2.94 (b, 2H), 3.1-3.7 (m, 15H), 6.65 (d, 1H), 7.72 (d, 1H), 6.86 (s, 1H), 7.19-7.33 (m, 5H), 8.90 (b, 1H), 11.8 (b, 2H).

EXAMPLE 2

1-[2-(3-Hydroxy-4-methoxyphenyl)ethyl]-4-(3-phenylpropyl)piperazine dihydrochloride

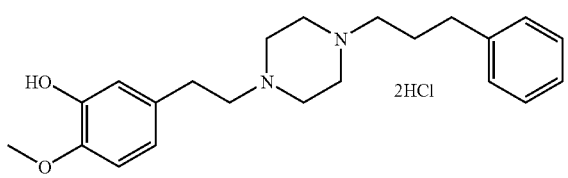

The title compound is prepared following the method of Example 1, but using 2-(3-hydroxy-4-methoxyphenyl)ethanamine hydrochloride instead of 2-(4-(benzyloxy)-3-methoxyphenyl)ethanamine hydrochloride.

m/z 355 [M+1]$^+$.

$^1$H-NMR (400 MHz, DMSO-d$_6$): δ 2.00 (b, 2H), 2.62 (t, 2H), 2.88 (m, 2H), 3.13 (m, 2H), 3.2-3.5 (b, mH, covered by water peak), 3.72 (b, 7H), 6.61-6.69 (m, 2H), 6.84 (d, 1H), 7.19-7.32 (m, 5H), 9.00 (b, 1H).

EXAMPLE 3

1-(2-Benzo[1,3]dioxol-5-ylethyl)-4-(3-phenylpropyl)piperazine dihydrochloride

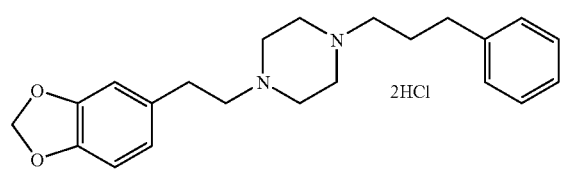

The title compound is prepared following the method of Example 1, but using 2-benzo[1,3]dioxol-5-ylethanamine instead of 2-(4-(benzyloxy)-3-methoxyphenyl)-ethanamine hydrochloride. m/z 353 [M+1]$^+$.

$^1$H-NMR (400 MHz, DMSO-d$_6$): δ 2.02 (b, 2H), 2.64 (t, 2H), 2.96 (b, 2H), 3.1-3.8 (m, 12H), 5.99 (s, 2H), 6.74 (d, 1H), 6.88 (m, 2H), 7.19-7.33 (m, 5H), 11.8 (b, 2H).

EXAMPLE 4

1-[2-(2-Fluorophenyl)ethyl]-4-(3-phenylpropyl)piperazine dihydrochloride

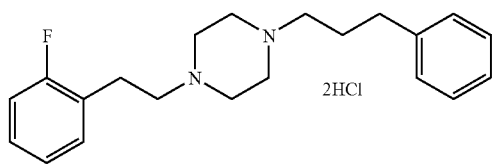

To a solution of bis(2-chloroethyl)-(3-phenylpropyl)ammonium chloride (0.593 g, 2 mmol) and 2-(2-fluorophenyl)ethanamine (0.278 g, 2 mmol) in dimethylformamide (6 mL) is added anhydrous potassium carbonate (0.829 g, 6 mmol) and sodium iodide (0.599 g, 4 mmol) successively. The reaction mixture is then stirred at 80° C. for 4.5 hours and then cooled to ambient temperature. Water and ethyl acetate are then added to the resultant reaction mixture. The organic layer is separated, washed 3 times with water and once with brine, dried over anhydrous magnesium sulfate, and concentrated. The residue is dissolved in ethanol. To this solution is added 6 N hydrochloric acid drop wise with cooling until pH 3. The resulting solution is maintained at 4° C. overnight. The resultant crystals are collected by filtration and washed with ethanol and ether to give 108 mg of the title compound (17%).

m/z 327 [M+1]$^+$.

$^1$H-NMR (400 MHz, DMSO-d$_6$): δ 2.04 (b, 2H), 2.65 (t, 2H), 3.1-3.8 (m, 14H), 7.17-7.41 (m, 9H), 77.9 (b, 21-1).

Anal. (C$_{21}$H$_{29}$Cl$_2$FN$_2$) C, 63.00; H, 7.53; Cl, 17.60; N, 6.97; Cal. C, 63.16; H, 7.32; Cl, 17.75; F, 4.76; N, 7.01.

EXAMPLE 5

1-[2-(3-Fluorophenyl)ethyl]-4-(3-phenylpropyl)piperazine dihydrochloride

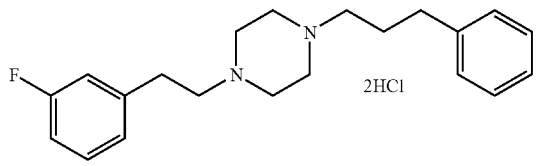

The title compound is prepared following the method of Example 4, but using 2-(3-fluorophenyl)ethanamine instead of 2-(2-fluorophenyl)ethanamine.

m/z 327 [M+1]$^+$.

¹H-NMR (400 MHz, DMSO-d$_6$): δ 2.04 (b, 2H), 2.65 (t, 2H), 3.1-3.8 (m, 14H), 7.03-7.41 (m, 9H), 11.8 (b, 2H).

EXAMPLE 6

1-[2-(4-Fluorophenyl)ethyl]-4-(3-phenylpropyl)piperazine dihydrochloride

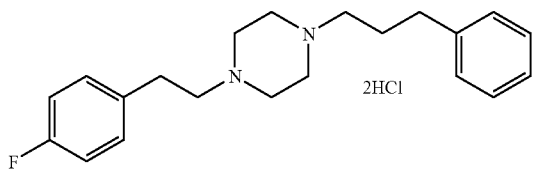

The title compound is prepared following the method of Example 4, but using 2-(4-fluorophenyl)ethanamine instead of 2-(2-fluorophenyl)ethanamine.

m/z 327 [M+1]$^+$.

¹H-NMR (400 MHz, DMSO-d$_6$): δ 2.03 (b, 2H), 2.64 (t, 2H), 3.0-3.8 (m, 14H), 7.14-7.35 (m, 9H), 11.8 (b, 2H).

EXAMPLE 7

1-[2-(3,4-Difluorophenyl)ethyl]-4-(3-phenylpropyl) piperazine dihydrochloride

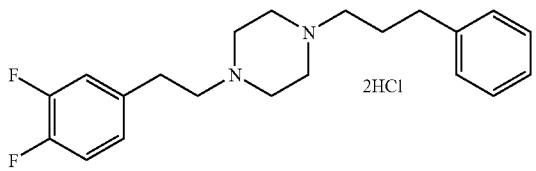

The title compound is prepared following the method of Example 4, but using 2-(3,4-difluorophenyl)ethanamine instead of 2-(2-fluorophenyl)ethanamine.

m/z 345 [M+1]$^+$.

¹H-NMR (400 MHz, DMSO-d$_6$): δ 2.03 (b, 2H), 2.65 (t, 2H), 3.06-3.75 (m, 14H), 7.14-7.45 (m, 8H), 11.8 (b, 2H).

EXAMPLE 8

1-[2-(3-Methylphenyl)ethyl]-4-(3-phenylpropyl) piperazine dihydrochloride

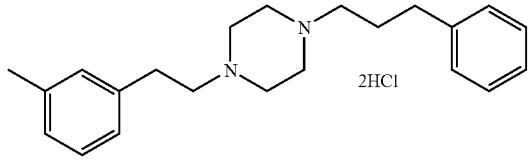

To the solution of bis(2-chloroethyl)-(3-phenylpropyl)ammonium chloride (1.78 g, 6 mmol) and 2-(3-methylphenyl)ethanamine (0.811 g, 6 mmol) in 8 mL of DMF is added anhydrous potassium carbonate (2.48 g, 18 mmol) and sodium iodide (1.80 g, 12 mmol) successively. The reaction mixture is then stirred at 80° C. for 4 hours and then cooled to ambient temperature. Water and ethyl acetate are then added to the resultant reaction mixture. The organic layer is separated, washed 3 times with water and once with brine, dried over anhydrous magnesium sulfate, and concentrated. The residue is dissolved in ethanol. To this solution is added 6 N hydrochloric acid drop wise with cooling until pH 3. The resulting solution is maintained at 4° C. overnight. The resultant crystals are collected by filtration and washed with ether to give 97 mg of the title compound (5%).

m/z 323 [M+1]$^+$.

¹H-NMR (400 MHz, DMSO-d$_6$): δ 2.03 (b, 2H), 2.29 (s, 3H), 2.65 (t, 2H), 3.0-3.8 (m, 14H), 7.08 (m, 3H), 7.18-7.34 (m, 6H), 11.8 (b, 2H).

Anal.: (C$_{22}$H$_{32}$N$_2$Cl$_2$ 0.5H$_2$O) C, 17.27; H, 8.25; Cl, 17.27; N, 6.97; Cal. C, 65.34; H, 8.22; Cl, 17.53; N, 6.93.

EXAMPLE 9

1-[2-(3-Trifluoromethylphenyl)ethyl]-4-(3-phenylpropyl)piperazine dihydrochloride

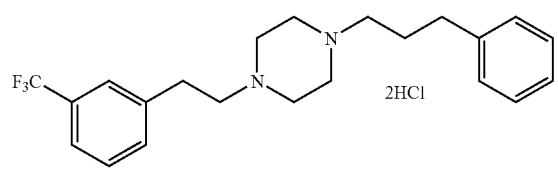

The title compound is prepared following the method of Example 4, but using 2-(3-trifluoromethylphenyl)ethanamine instead of 2-(2-fluorophenyl)ethanamine.

m/z 377 [M+1]$^+$.

¹H-NMR (400 MHz, DMSO-d$_6$) δ 2.04 (b, 2H), 2.65 (t, 2H), 3.19 (b, 4H), 3.3-3.8 (m, 10H), 7.19-7.34 (m, 5H), 7.56-7.71 (m, 4H), 11.8 (b, 2H).

EXAMPLE 10

1-[2-(2-Trifluoromethoxyphenyl)ethyl]-4-(3-phenylpropyl)piperazine dihydrochloride

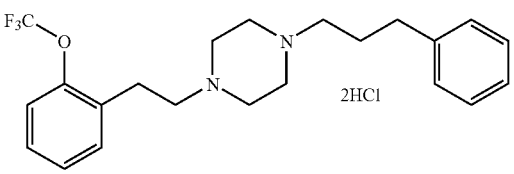

The title compound is prepared following the method of Example 4, but using 2-(2-trifluoromethoxyphenyl)ethanamine instead of 2-(2-fluorophenyl)ethanamine.

m/z 393 [M+1]$^+$.

¹H-NMR (400 MHz, DMSO-d₆): δ 2.04 (b, 2H), 2.65 (t, 2H), 3.1-3.8 (m, 14H), 7.2-7.7 (m, 9H), 11.8 (b, 2H).

EXAMPLE 11

1-[2-(3-Chloro-4-methoxyphenyl)ethyl]-4-(3-phenylpropyl)piperazine dihydrochloride

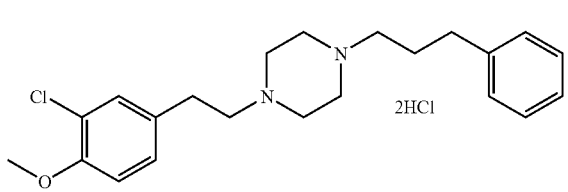

The title compound is prepared following the method of Example 4, but using 2-(3-chloro-4-methoxyphenyl)ethanamine instead of 2-(2-fluorophenyl)ethanamine.

m/z 373 [M+1]⁺.

¹H-NMR (400 MHz, DMSO-d₆): δ 2.03 (b, 2H), 2.65 (t, 2H), 2.99 (b, 2H), 3.1-3.9 (m, 15H), 7.11 (d, 1H), 7.22 (m, 4H), 7.32 (t, 2H), 7.39 (t, 1H), 11.8 (b, 2H).

EXAMPLE 12

1-(R)-Indan-1-yl-4-(3-phenylpropyl)piperazine dihydrochloride

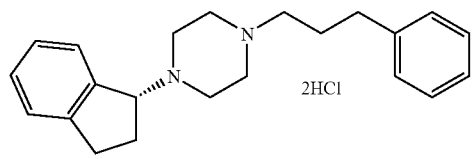

The title compound is prepared following the method of Example 4, but using (R)-indan-1-ylamine instead of 2-(2-fluorophenyl)ethanamine.

m/z 321 [M+1]⁺.

¹H-NMR (400 MHz, DMSO-d₆): δ 1.98 (b, 2H), 2.41 (b, 1H), 2.63 (t, 2H), 2.90 (b, 1H0, 3.11 (b, 3H), 3.3-3.7 (m, 9H), 7.18-7.40 (m, 8H), 7.79 (s, 1H), 11.7 (b, 1H), 11.4 (b, 1H).

EXAMPLE 13

1-[(S)-(1-Methoxymethyl-2-phenyl)ethyl]-4-(3-phenylpropyl)piperazine dihydrochloride

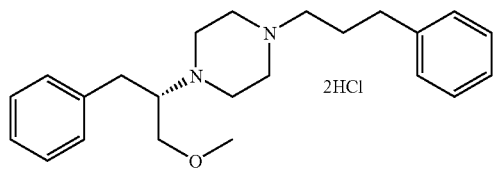

The title compound is prepared following the method of Example 4, but using (S)-1-methoxy-3-phenylprop-2-ylamine instead of 2-(2-fluorophenyl)ethanamine.

m/z 353 [M+1]⁺.

¹H-NMR (400 MHz, DMSO-d₆): δ 2.03 (b, 2H), 2.66 (t, 2H), 2.91 (b, 1H), 3.1-3.8 (m, 17H), 7.1-7.4 (m, 10H), 11.9 (b, 2H).

EXAMPLE 14

1-[2-(2-Chloro-6-fluorophenyl)ethyl]-4-(3-phenylpropyl)-piperazine dihydrochloride

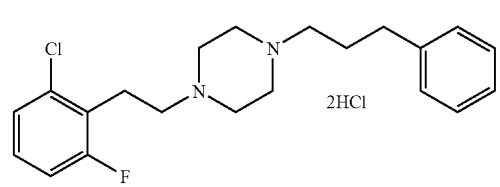

The title compound is prepared following the method of Example 4, but using 2-(2-chloro-6-fluorophenyl)ethanamine instead of 2-(2-fluorophenyl)ethanamine.

m/z 361 [M+1]⁺

¹H-NMR (400 MHz, DMSO-d₆): δ 2.03 (b, 2H), 2.65 (t, 2H), 3.1-3.8 (m, 14H), 7.2-7.4 (m, 8H), 11.6 (b, 2H).

EXAMPLE 15

1-[2-(3,4-Dihydroxyphenyl)ethyl]-4-(3-phenylpropyl)piperazine dihydrochloride

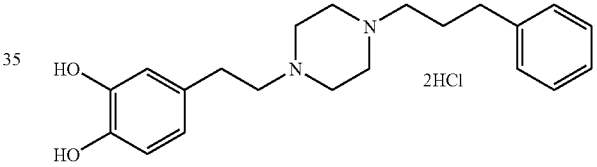

1-[2-(3,4-Dimethoxyphenyl)ethyl]-4-(3-phenylpropyl)piperazine dihydrochloride is prepared following the method of Example 4, but using 2-(3,4-dimethoxyphenyl)ethanamine instead of 2-(2-fluorophenyl)ethanamine.

To a suspension of 1-[2-(3,4-dimethoxyphenyl)ethyl]-4-(3-phenylpropyl)piperazine dihydrochloride (1.06 g, 2.40 mmol) in THF (5 mL) is added a solution of sodium hydroxide (1N, 6 mL). To the resulting solution is added ethyl acetate and brine. The organic layer is separated, filtered through silica gel, dried over anhydrous sodium sulfate, concentrated, and dried to give 0.829 g of 1-[2-(3,4-dimethoxyphenyl)ethyl]-4-(3-phenylpropyl)piperazine as a light brown solid.

To a solution of 1-[2-(3,4-dimethoxyphenyl)ethyl]-4-(3-phenylpropyl)piperazine (0.829 g, 2.25 mmol) in dichloromethane (DCM, 20 mL) is added boron tribromide (BBr₃) drop wise at −78° C. under nitrogen. After the addition had been completed, the reaction solution is slowly warmed to 0° C., stirred for 5 h and then cooled to −10° C. To the cooled reaction mixture is added water cautiously. The resulting mixture is neutralised with sodium bicarbonate at ambient temperature and extracted with ethyl acetate/THF. The organic layer is separated, filtered through silica gel, dried over sodium sulfate, concentrated, and dried in a vacuum oven. The residue is then purified by column chromatography eluting with dichloromethane-methanol to afford 0.57 g of 1-[2-(3,4-dihydroxyphenyl)ethyl]-4-(3-phenylpropyl)piperazine. This material is then dissolved in ethanol and treated with 6 N hydrogen chloride aqueous solution to pH=3. The resultant crystals are filtered, washed with cold ethanol, and dried to give 212 mg of the title compound (25% from 1-[2-(3,4-dimethoxyphenyl)ethyl]-4-(3-phenylpropyl)piperazine dihydrochloride).

m/z 355 [M+1]$^+$.

$^1$H-NMR (400 MHz, DMSO-d$_6$): δ 2.02 (b, 2H), 2.64 (t, 2H), 2.86 (b, 2H), 3.1-3.8 (m, 12), 6.51 (d, 1H), 6.67 (m, 2H), 7.11-7.33 (m, 5H), 8.84 (b, 2H), 11.6 (b, 2H).

Other compounds which could be prepared using the method described in Example 4, starting from the appropriate ethanamine include:

1-[2-(2-Methoxyphenyl)ethyl]-4-(3-phenylpropyl)piperazine dihydrochloride;
1-[2-(2-Fluoro-3,4-dimethoxyphenyl)ethyl]-4-(3-phenylpropyl)piperazine dihydrochloride;
1-[2-(2,3,4-Trimethoxyphenyl)ethyl]-4-(3-phenylpropyl)piperazine dihydrochloride;
1-[2-(2-Trifluoromethylphenyl)ethyl]-4-(3-phenylpropyl)piperazine dihydrochloride;
1-[2-(4-Trifluoromethylphenyl)ethyl]-4-(3-phenylpropyl)piperazine dihydrochloride;
1-[2-(3-Trifluoromethoxyphenyl)ethyl]-4-(3-phenylpropyl)piperazine dihydrochloride;
1-[2-(3-Chlorophenyl)ethyl]-4-(3-phenylpropyl)piperazine dihydrochloride;
1-[2-(2-Fluoro-4,5-dimethoxyphenyl)ethyl]-4-(3-phenylpropyl)piperazine dihydrochloride;
1-[2-(2-Fluoro-4-methoxy-5-hydroxyphenyl)ethyl]-4-(3-phenylpropyl)piperazine dihydrochloride;
1-[2-(3-Bromo-4,5-dimethoxyphenyl)ethyl]-4-(3-phenylpropyl)piperazine dihydrochloride;
1-[2-(3-Bromo-4-ethoxy-5-methoxyphenyl)ethyl]-4-(3-phenylpropyl)piperazine dihydrochloride;
1-[2-(3-Bromo-4-methoxy-5-ethoxyphenyl)ethyl]-4-(3-phenylpropyl)piperazine dihydrochloride;
1-[2-(3-Methoxy-4-isopropoxyphenyl)ethyl]-4-(3-phenylpropyl)piperazine dihydrochloride;
1-[2-(3-Fluoro-4,5-dimethoxyphenyl)ethyl]-4-(3-phenylpropyl)piperazine dihydrochloride;
1-[2-(3,5-Dimethoxy-4-hydroxyphenyl)ethyl]-4-(3-phenylpropyl)piperazine dihydrochloride;
1-[2-(3-Bromo-4-hydroxy-5-methoxyphenyl)ethyl]-4-(3-phenylpropyl)piperazine dihydrochloride;
1-[2-(3,4-Dimethoxy-5-hydroxyphenyl)ethyl]-4-(3-phenylpropyl)piperazine dihydrochloride;
1-[2-(2-Chloro-3,4-dimethoxyphenyl)ethyl]-4-(3-phenylpropyl)piperazine dihydrochloride;
1-[2-(3-Isopropyl-4-methoxyphenyl)ethyl]-4-(3-phenylpropyl)piperazine dihydrochloride;
1-[2-(7-Fluorobenzo[1,3]dioxol-5-yl]ethyl]-4-(3-phenylpropyl)piperazine dihydrochloride;
1-[2-(3-Chloro-4-methoxy-5-isopropylphenyl)ethyl]-4-(3-phenylpropyl)piperazine dihydrochloride;
1-[2-(4-Cyclohexyl-3-methoxyphenyl)ethyl]-4-(3-phenylpropyl)piperazine dihydrochloride;
1-[2-(2-Chloro-3-methoxy-4-hydroxyphenyl)ethyl]-4-(3-phenylpropyl)piperazine dihydrochloride;
1-Indan-2-yl-4-(3-phenylpropyl)piperazine dihydrochloride;
1(S)-Indan-1-yl-4-(3-phenylpropyl)piperazine dihydrochloride;
1-(1R,2S)-(2-Hydroxyindan-1-yl)-4-(3-phenylpropyl)piperazine dihydrochloride;
1-(1S,2R)-(2-Hydroxyindan-1-yl)-4-(3-phenylpropyl)piperazine dihydrochloride;
1-(1R)-(1,2,3,4-Tetrahydronaphthalen-1-yl)-4-(3-phenylpropyl)piperazine dihydrochloride;
1-(1S)-(1,2,3,4-Tetrahydronaphthalen-1-yl)-4-(3-phenylpropyl)piperazine dihydrochloride;
1-Cyclopentyl-4-(3-phenylpropyl)piperazine dihydrochloride; and
1-(1S,2S)-(2-Hydroxycyclopentyl)-4-(3-phenylpropyl)piperazine dihydrochloride.

The invention claimed is:

1. A compound of general formula (I)

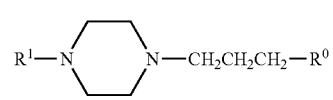

(I)

in which:—

R$^0$ represents phenyl or 4-fluorophenyl; and
R$^1$ represents:—
(i) a group of formula

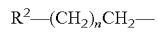

wherein:
n is 1 or 2; and
R$^2$ represents a phenyl group that is substituted by one fluorine atom or phenyl substituted by one, two, or three substituents selected independently from (1-2C)alkylenedioxy, a hydroxyl group, a (1-4C) alkyl group, a (3-6C)cycloalkyl group, and a halo(1-4C) alkyl group; or
(ii) a group of formula

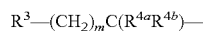

wherein:
m is 1 or 2; and
R$^3$ represents a phenyl group that is unsubstituted or substituted by one, two or three substituents selected independently from (1-2C)alkylenedioxy, a halogen atom, a hydroxyl group, a (1-4C) alkyl group, a (3-6C)cycloalkyl group, a halo(1-4C) alkyl group, a (1-4C) alkoxy group and a halo(1-4C)alkoxy group; and
one or two of R$^{4a}$ and R$^{4b}$ represents a (1-4C) alkyl or a (1-4C)alkoxy(1-4C)alkyl group and any remainder represents a hydrogen atom; or
(iii) indan-1-yl, indan-2-yl, 1,2,3,4-tetrahydronaphth-1-yl or 1,2,3,4-tetrahydronaphth-2-yl, each of which may bear a hydroxyl substituent on a non-aromatic carbon atom; or (3-6C) cycloalkyl;
or a pharmaceutically acceptable salt thereof.

2. A compound of general formula (I)

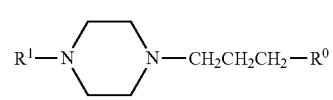

(I)

in which:—

R$^0$ represents phenyl or 4-fluorophenyl; and
R$^1$ represents indan-1-yl, indan-2-yl, 1,2,3,4-tetrahydronaphth-1-yl, or 1,2,3,4-tetrahydronaphth-2-yl, each of which may bear a hydroxyl substituent on a non-aromatic carbon atom; or (3-6C) cycloalkyl.

3. A compound according to claim 2, in which R$^1$ represents indan-1-yl.

4. A compound according to claim 3 selected from the group consisting of 1(R)-Indan-1-yl-4-(3-phenylpropyl)piperazine;

1(S)-Indan-1-yl-4-(3-phenylpropyl)piperazine ;

1-(1R, 2S)-(2-Hydroxyindan-1-yl)-4-(3-phenylpropyl) piperazine;

1-(1S, 2R)-(2-Hydroxyindan-1-yl)-4-(3-phenylpropyl) piperazine; and pharmaceutically acceptable salts thereof.

5. A compound according to claim 4 in the form of a dihydrochloride salt.

6. A compound according to claim 3 which is 1(R)-Indan-1-yl-4-(3-phenylpropyl)piperazine dihydrochloride.

7. A compound according to claim 2 in which $R^1$ represents indan-2-yl.

8. A compound according to claim 7 which is 1(R)-Indan-2-yl-4-(3-phenylpropyl)piperazine, 1(S)-Indan-2-yl-4-(3-phenylpropyl)piperazine, or a pharmaceutically acceptable salt thereof.

9. A pharmaceutical composition, which comprises a therapeutically effective amount of a compound of general formula (I)

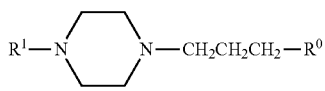

in which:—

$R^0$ represents phenyl or 4-fluorophenyl; and $R^1$ represents:—

(i) a group of formula

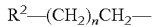

wherein:

n is 1 or 2; and $R^2$ represents a phenyl group that is substituted by one fluorine atom or phenyl substituted by one, two, or three substituents selected independently from (1-2C)alkylenedioxy, a hydroxyl group, a (1-4C) alkyl group, a (3-6C)cycloalkyl group, and a halo(1-4C) alkyl group; or (ii) a group of formula

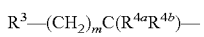

wherein:

m is 1 or 2; and $R^3$ represents a phenyl group that is unsubstituted or substituted by one, two or three substituents selected independently from (1-2C)alkylenedioxy, a halogen atom, a hydroxyl group, a (1-4C) alkyl group, a (3-6C)cycloalkyl group, a halo(1-4C) alkyl group, a (1-4C) alkoxy group and a halo(1-4C)alkoxy group; and one or two of $R^{4a}$ and $R^{4b}$ represents a (1-4C) alkyl or a (1-4C)alkoxy(1-4C)alkyl group and any remainder represents a hydrogen atom; or (iii) indan-1-yl, indan-2-yl, 1,2,3,4-tetrahydronaphth-1-yl or 1,2,3,4-tetrahydronaphth-2-yl, each of which may bear a hydroxyl substituent on a non-aromatic carbon atom; or (3-6C) cycloalkyl;

or a pharmaceutically acceptable salt thereof, and a pharmaceutically acceptable diluent or carrier.

10. A pharmaceutical composition, which comprises a compound of general formula (I)

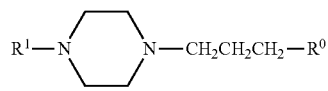

in which:—

$R^0$ represents phenyl or 4-fluorophenyl; and $R^1$ represents indan-1-yl, indan-2-yl, 1,2,3,4-tetrahydronaphth-1-yl, or 1,2,3,4-tetrahydronaphth-2-yl, each of which may bear a hydroxyl substituent on a non-aromatic carbon atom; or (3-6C) cycloalkyl, or a pharmaceutically acceptable salt thereof, and a pharmaceutically acceptable diluent or carrier.

11. The pharmaceutical composition according to claim 10, in which in the compound of general formula (I) $R^1$ represents indan-1-yl or indan-2-yl.

12. The pharmaceutical composition according to claim 10, in which in the compound of general formula (I) is selected from 1(R)-Indan-1-yl-4-(3-phenylpropyl)piperazine;

1(S)-Indan-1-yl-4-(3-phenylpropyl)piperazine;

1-(1R, 2S)-(2-Hydroxyindan-1-yl)-4-(3-phenylpropyl) piperazine;

1-(1S, 2R)-(2-Hydroxyindan-1-yl)-4-(3-phenylpropyl) piperazine; and pharmaceutically acceptable salts thereof, in combination with a pharmaceutically acceptable diluent or carrier.

13. The pharmaceutical composition according to claim 10, in which in the compound of general formula (I) is selected from 1(R)-Indan-2-yl-4-(3-phenylpropyl)piperazine, 1(S)-Indan-2-yl-4-(3-phenylpropyl)piperazine, and a pharmaceutically acceptable salt thereof, in combination with a pharmaceutically acceptable diluent or carrier.

* * * * *